United States Patent
Star

(10) Patent No.: US 6,209,543 B1
(45) Date of Patent: Apr. 3, 2001

(54) CONDOM PROVIDING ENHANCED PROTECTION AGAINST SEXUALLY TRANSMITTED DISEASES

(76) Inventor: Carol W. Star, 2333 Kapiolani Blvd. Suite. 1213, Honolulu, HI (US) 96826

(*) Notice: Subject to any disclaimer, the term of this patent is extended or adjusted under 35 U.S.C. 154(b) by 0 days.

(21) Appl. No.: 09/476,044

(22) Filed: Dec. 31, 1999

Related U.S. Application Data

(60) Provisional application No. 60/144,299, filed on Jul. 16, 1999.

(51) Int. Cl.$^7$ ...................................... A61F 6/04
(52) U.S. Cl. ........................................ 128/844; 128/918
(58) Field of Search ........................ 128/842, 844, 128/918; 604/347–353

(56) References Cited

U.S. PATENT DOCUMENTS

| | | | |
|---|---|---|---|
| 3,759,254 | * 9/1973 | Clark | 128/844 |
| 3,990,119 | 11/1976 | Barrett | 4/1 |
| 4,009,717 | * 3/1977 | Allen | 604/347 |
| 4,354,494 | 10/1982 | Hogin | 128/294 |
| 4,381,000 | 4/1983 | Duncan | 128/79 |
| 4,590,931 | 5/1986 | Kidwell, Jr. | 128/162 |
| 4,627,846 | 12/1986 | Ternstrom | 604/349 |
| 5,063,939 | 11/1991 | Walston | 128/842 |
| 5,070,890 | 12/1991 | Papurt | 128/844 |
| 5,111,831 | 5/1992 | Foggia | 128/842 |
| 5,113,873 | * 5/1992 | Boarman | 128/844 |
| 5,156,165 | 10/1992 | Wu | 128/844 |
| 5,314,447 | 5/1994 | Papurt | 128/842 |
| 5,318,042 | 6/1994 | Gray | 128/844 |
| 5,351,699 | 10/1994 | Hammons | 128/844 |
| 5,370,130 | 12/1994 | Hess | 128/844 |
| 5,370,131 | 12/1994 | Hess | 128/844 |
| 5,398,699 | 3/1995 | Fergus | 128/844 |
| 5,513,653 | 5/1996 | Huang | 128/842 |
| 5,618,279 | 4/1997 | Pudlo | 604/385.1 |
| 5,666,971 | * 9/1997 | Anatolievich | 128/844 |
| 5,715,839 | 2/1998 | Strauss et al. | 128/842 |
| 5,716,350 | 2/1998 | Ryan | 604/385.1 |
| 5,718,236 | * 2/1998 | Curico | 128/844 |
| 5,855,206 | * 1/1999 | Ireland | 128/844 |

* cited by examiner

Primary Examiner—Michael A. Brown
(74) Attorney, Agent, or Firm—James J. Leary; Carol D. Titus

(57) ABSTRACT

A reliable male condom that is roughly tubular and that has one open end and one closed end and that applies to the purposes of disease prevention and birth control. A fitted scrotal sac extends downward from the bottom portion of the open end and extends partly up the shaft. A restraining strap, optionally attached and with fixable ends, is wrapped around the periphery of the open end, guided by a finishing lip or band, in order to secure the scrotum within the scrotal sac and also to anchor the condom during use. For increased stability, an optional restrictive band is also provided. In a modified form, the scrotal sac is semi-fitted to the scrotum, and in another form, the scrotal sac is unfitted, and the restrictive band is not provided. All forms provide an optional reservoir tip.

18 Claims, 4 Drawing Sheets

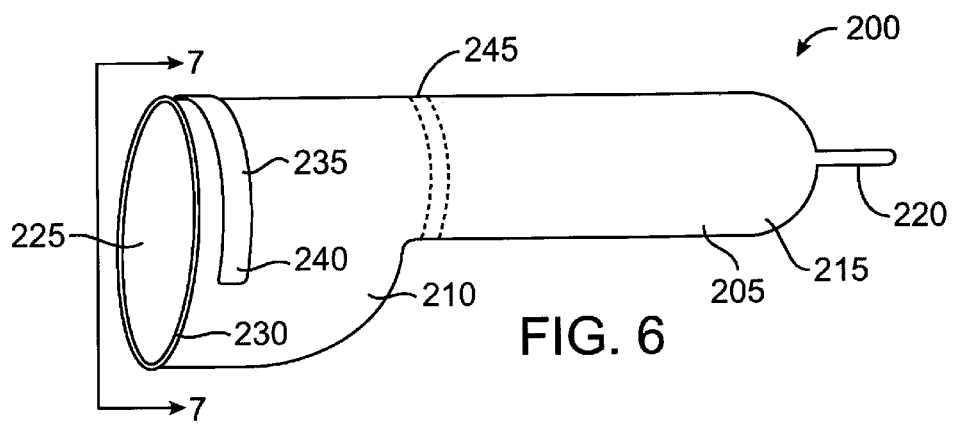
FIG. 6
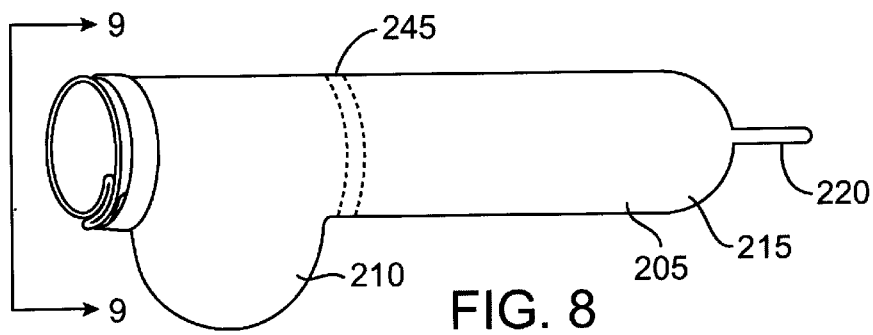
FIG. 8
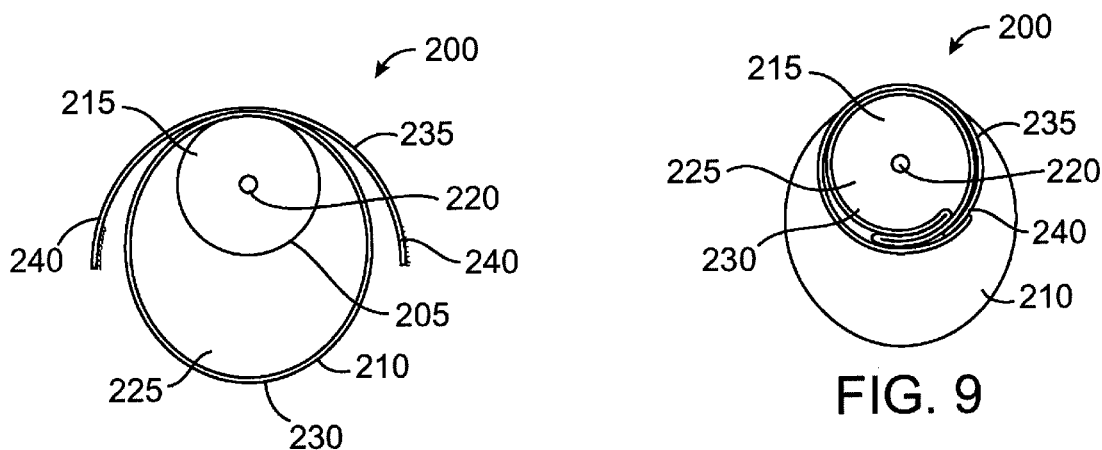
FIG. 7
FIG. 9
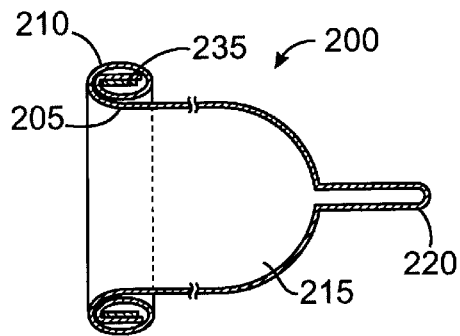
FIG. 10

CONDOM PROVIDING ENHANCED PROTECTION AGAINST SEXUALLY TRANSMITTED DISEASES

CROSS REFERENCE TO OTHER APPLICATIONS

This application claims the benefit of U.S. Provisional Patent Application No. 60/144,299, filed Jul. 16, 1999.

FIELD OF THE INVENTION

The present invention relates to an improved male condom intended to effectively protect sexually active men and women at risk of contracting one of the twenty or more known sexually transmitted diseases (STDs) prevalent today in populations throughout the U.S. and worldwide. More specifically, it relates to a roughly tubular, non-continuous shaft that covers the entire penis and scrotum of the male and that uses a restraining strap and a restrictive band to minimize slippage, thus providing comprehensive and reliable protection against disease and pregnancy.

BACKGROUND OF THE INVENTION

Sexually transmitted diseases (STDs) continue to spread at an alarming rate throughout the U.S. population. In fact, it is estimated that 12 million people in the U.S. acquire some form of STD each year. Overall, about one in four Americans have an STD. This category includes such conditions as herpes, syphilis, gonorrhea, trichomoniasis, chlamydia and HIV (AIDS), among others. STDs are most commonly spread when sexual partners engage in unprotected sex, that is, the infected genitalia (and surrounding area) of one partner comes into contact with the genitalia (and surrounding area) of another partner, thus transferring the infection. Although most STDs respond to some form of treatment, certain sexually transmitted pathogens cause cervical, liver, and other cancers, while infections in pregnant women can cause spontaneous abortion, stillbirth, pre-term delivery, and illness among infants.

The object of this invention is to provide sexual partners with effective protection against both STDs and unintended pregnancy. This has been accomplished by fashioning a male condom with a scrotal sac or pouch with an optionally removable restraining strap. Together, the sac and strap are intended to provide improved prophylactic and contraceptive protection when compared with a traditional continuous shaft condom that does not include scrotal coverage or restraining capability. The scrotal sac provides more comprehensive protection against disease by preventing contact between the scrotum and the labia, and between the scrotum and the anal region. The restraining strap provides more reliable protection against disease and pregnancy in that it anchors the condom, thus safeguarding against the condom slipping partly or completely off during sexual intercourse, a consequence known to occur with traditional, continuous shaft condoms used by most condom users throughout the U.S. and worldwide today. To further increase protection against slippage, the shaft portion of the condom includes an optional restrictive band.

This invention is an advancement over prior art patents of a similar construction in two important ways: (1) the construction of the scrotal sac, designed for improved admittance and accommodation of the scrotum; and (2) the introduction of a restraining strap with fixable ends, intended to anchor the condom and to prevent slippage during sexual intercourse.

For example, U.S. Pat. No. 5,070,890 and U.S. Pat. No. 5,314,447 include a scrotal sac in each embodiment, but the sac opening has the disadvantages of not being substantially wider than the shaft and of not being fashioned from a pliant construction, hindering admittance of the scrotum into the scrotal sac. And since condom usage is often dependent on convenience and comfort, this limitation could discourage usage, possibly during a sexual encounter where usage is necessary to prevent disease and/or pregnancy.

Likewise, U.S. Pat. No. 5,718,236 and U.S. Pat. No. 5,318,042 have the disadvantages of limited access and rigid construction relative to the scrotal sac. Moreover, these patents do not provide a restraining mechanism to prevent the condom from slipping partly or completely off during sexual intercourse as does the present invention.

U.S. Pat. No. 4,354,494 does provide a restraining strap that fits over the scrotum. However, it is unclear if this strap would remain secure during sexual intercourse and if tension from this strap would cause discomfort to the testes, whereas the restraining strap of the present invention is designed to provide a comfortable, secure fit. Also significant, this patent does not provide a reservoir tip. Therefore, it is unable to provide the same level of protection as the present invention.

SUMMARY OF THE INVENTION

The condom of the present invention provides an improved prophylactic and birth control device comprising a tubular shaft portion that is roughly cylindrical and that covers the shaft of the penis and a scrotal portion that covers the scrotum. Preferably, the condom is made of latex, polyurethane, rubber or other polymer or elastomer fashioned into a non-rigid, pliant construction. The condom is closed at one end and includes an optional reservoir tip for containing semen, and is open at the other end for admitting the penis and the scrotum. The periphery of the open end is preferably finished with a lip or band. The scrotal portion includes a scrotal sac or pouch that extends downward from the flexible open end, so that once the penis is effectively fitted into the tubular shaft portion, the scrotum easily and comfortably enters the scrotal sac. A restraining strap, which is optionally separate or removable, is comprised of a relatively flat elastic material with fixable ends that, when fastened, serve to enclose the scrotum in the scrotal sac and to anchor the condom onto the user. Specifically, with the penis first extended into the shaft and the scrotal sac loosely fitted around the scrotum, the strap is properly applied by grasping each hanging end with the index finger and thumb of each hand, then pulling each end up in opposite directions while following the periphery or lip of the open end, securing the scrotum within the sac, then finally, fastening the ends at the top of the shaft, just inside the lip or band, with a VELCRO hook-and-loop fastener or a similar fastening agent intended to effectively anchor the condom during even vigorous sexual activity. Also, for additional protection against slippage, the tubular shaft includes an optional restrictive band located between the scrotal sac and shaft portion of the condom.

BRIEF DESCRIPTION OF THE DRAWINGS

FIG. 6 is a side view of a semi-fitted version of the condom of the present invention, shown in an unfastened state.

FIG. 7 is a proximal end view of the semi-fitted condom of FIG. 6 in the unfastened state.

FIG. 8 is a side view of the semi-fitted condom of FIG. 6, shown in a fastened state.

FIG. 9 is a proximal end view of the semi-fitted condom of FIG. 8 in the fastened state.

FIG. 10 is a cross section of the semi-fitted condom of FIG. 6, shown in a rolled state for storage or application.

DETAILED DESCRIPTION OF THE INVENTION

Figure 1:
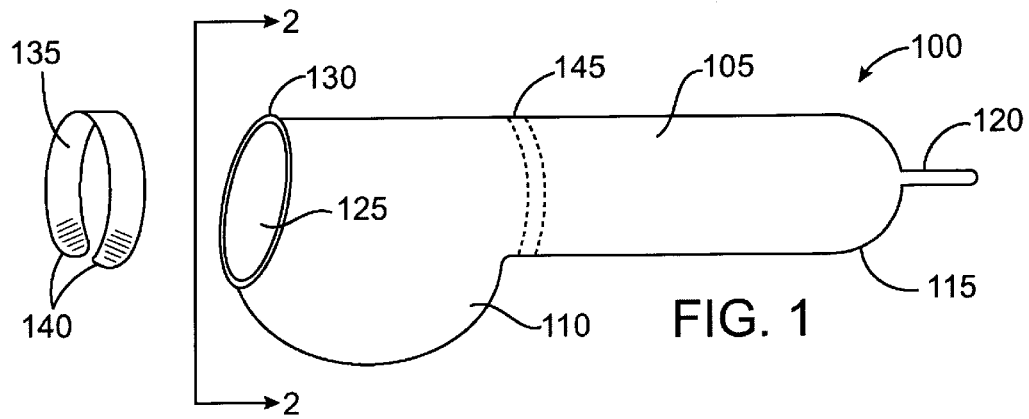
FIG. 1 is a side view of a fitted version of the condom of the present invention, shown in an unfastened state.
Figure 2:
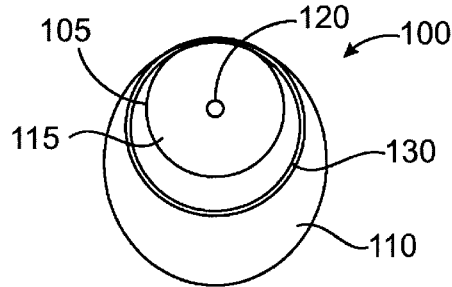
FIG. 2 is a proximal end view of the fitted condom of FIG. 1 in the unfastened state.

FIGS. 1 through 5 illustrate a first preferred embodiment of the present invention, which is a fitted version of a condom 100 configured to cover a user's penis and scrotum. FIG. 1 is a side view of the fitted condom 100 in an unfastened state. FIG. 2 is a proximal end view of the fitted condom 100 of FIG. 1 in the unfastened state. The condom 100 is constructed with a roughly tubular shaft 105 that is attached at its proximal end to a scrotal sac 110. The scrotal sac 110 is asymmetrical with the tubular shaft 105 in keeping with the normal anatomical configuration of the male genitalia. When properly fitted, the tubular shaft 105 covers the entire penis and the scrotal sac 110 covers the entire scrotum. The condom 100 has one closed end 115 at the distal end of the tubular shaft 105 that includes an optional reservoir tip 120 for containing semen, and one open end 125 at the proximal end of the scrotal sac 110 for admitting the user's penis and the scrotum.

The scrotal sac 110 is sized to loosely and comfortably fit the user's scrotum and testicles without discomfort or constriction. The open end 125 of the condom 100 is sized to easily and comfortably admit the user's scrotum and testicles into the scrotal sac 110 without discomfort or constriction and without any need to stretch the opening 125. In this embodiment, the open end 125 of the fitted condom 100 is preferably somewhat smaller than the maximum diameter of the scrotal sac 110, but larger than the diameter of the tubular shaft 105. The periphery of the open end 125 is preferably finished with a lip or band 130 that is distinctly rounded and extends slightly above the surface of the tubular shaft 105 and that provides a useful gripping surface for helping to apply the condom 100 over the surface of the penis. In one preferred embodiment, the lip or band 130 around the open end 125 of the scrotal sac 110 is approximately 1 mm thick.

Preferably, the condom 100 is made of a highly flexible and elastic polymer or elastomer. Suitable materials include, but are not limited to latex, polyurethane and other natural and synthetic rubbers. Preferably, the tubular shaft 105 and the scrotal sac 110 of the condom 100 are manufactured together in one piece, such as by dip molding, out of a single material. Alternatively, however, the tubular shaft 105 and the scrotal sac 110 may be made of different materials and joined together, for instance by adhesive bonding or by heat welding. Additionally or alternatively, natural membranes or textile fabrics may be used in the construction of the tubular shaft 105 and/or scrotal sac 110 of the condom 100.

The fitted condom 100 also includes a restraining strap 135 that, when fastened, secures the scrotum within the scrotal sac 110 and effectively anchors the condom 100 during use. The restraining strap 135 is preferably constructed of a relatively flat elastic material and has fixable ends 140. The fixable ends 140 of the restraining strap 135 include a fastener, such as corresponding halves of a VEL-CRO hook-and-loop fastener strip or a similarly effective fastener or an adhesive. In this illustrative embodiment, the restraining strap 135 is shown as separate from the condom 100. Optionally, however, the restraining strap 135 may be permanently or removably attached to the condom 100 near the open end 125. The restraining strap 135 is preferably sized to fasten the open end 125 of the scrotal sac 110 snuggly and comfortably around the user proximal to the scrotum. In one preferred embodiment, the restraining strap 135 is approximately 1 cm wide, 10 cm long, and 1 mm thick. The lip or band 130 around the open end 125 of the scrotal sac 110 serves as a stopper ring to prevent the fastened restraining strap 135 from slipping off of the condom 100.

Figure 3:
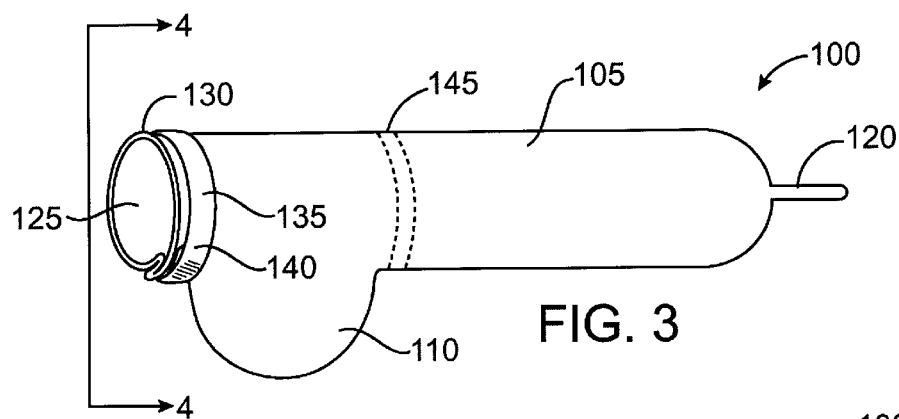
FIG. 3 is a side view of the fitted condom of FIG. 1, shown in a fastened state.

For additional protection against slippage, the condom 100 may optionally include a restrictive band 145, indicated by dashed lines in FIGS. 1 and 3, around the periphery of the tubular shaft 105. The restrictive band 145 is preferably located at the proximal end of the tubular shaft 105 where it joins to the scrotal sac 110. The restrictive band 145 may be formed by a slight thickening of the wall of the tubular shaft 105 and/or by a slight reduction in the internal diameter of the tubular shaft 105.

Figure 4:
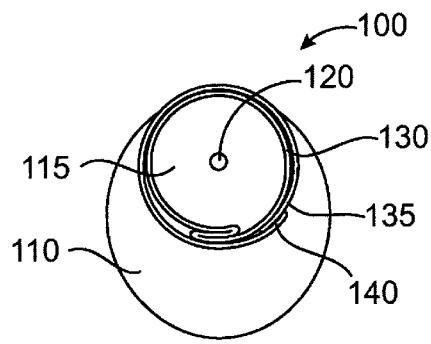
FIG. 4 is a proximal end view of the fitted condom of FIG. 3 in the fastened state.
Figure 5:
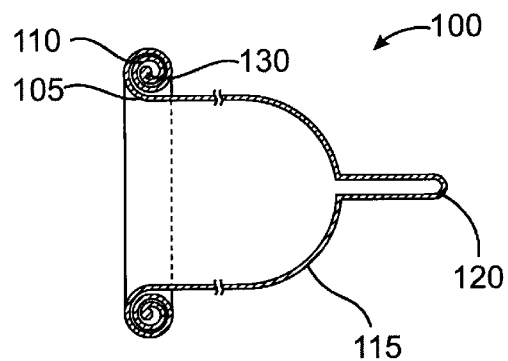
FIG. 5 is a cross section of the fitted condom of FIG. 1, shown in a rolled state for storage or application.

FIG. 3 illustrates the condom 100 of FIG. 1 fastened and shows the restraining strap 135 properly positioned just distal to the finishing lip or band 130 of the open end 125 and with each fixable end 140 properly adhered to the surface of the condom. FIG. 4 illustrates the proximal end view of the fitted condom and shows the folds of material that gather at the underside of the open end 125 when the restraining strap 135 is applied. FIG. 5 illustrates that this embodiment of the condom 100 can optionally be rolled for storage or application. The condom 100 can be packaged, rolled or unrolled, in a plastic or foil pouch for storage, sales and distribution.

FIGS. 6 through 10 illustrate a second preferred embodiment of the present invention, which is a semi-fitted version of a condom 200 configured to cover a user's penis and scrotum. FIG. 6 is a side view of the semi-fitted condom 200 in an unfastened state. FIG. 7 is a proximal end view of the semi-fitted condom 200 of FIG. 6 in the unfastened state. The semi-fitted condom 200 is constructed with a roughly tubular shaft 205 that is attached at its proximal end to a scrotal sac 210, and with a closed distal end 215 and an open proximal end 225, similar to the fitted version previously described. However, in this embodiment, the scrotal sac 210 fits more relaxed and is less form-fitting around the scrotum, hence the designation semi-fitted. In this embodiment, the open end 225 of the semi-fitted condom 200 preferably represents the maximum diameter of the scrotal sac 210, and is significantly larger than the diameter of the tubular shaft 205. The scrotal sac 210 is asymmetrical with the tubular shaft 205 in keeping with the normal anatomical configuration of the male genitalia. When properly fitted, the tubular shaft 205 covers the entire penis and the scrotal sac 210 covers the entire scrotum.

Preferably, the condom 200 is made of a highly flexible and elastic polymer or elastomer, including, but not limited to latex, polyurethane and other natural and synthetic rubbers. Preferably, the tubular shaft 205 and the scrotal sac 210 of the condom 200 are manufactured together in one piece, such as by dip molding, out of a single material. Alternatively, however, the tubular shaft 205 and the scrotal sac 210 maybe made of different materials and joined together, for instance by adhesive bonding or by heat welding. Additionally or alternatively, natural membranes or textile fabrics may be used in the construction of the tubular shaft 205 and/or scrotal sac 210 of the condom 200.

The semi-fitted condom 200 also includes a restraining strap 235 that, when fastened, secures the scrotum within the scrotal sac 210 and effectively anchors the condom 200 during use. FIGS. 6 and 7 illustrate the restraining strap 235 in position, but not fastened. The restraining strap 235 is preferably constructed of a relatively flat elastic material and has fixable ends 240. The fixable ends 240 of the restraining strap 235 include a fastener, such as corresponding halves of a VELCRO hook-and-loop fastener strip, or an adhesive. In this illustrative embodiment, the restraining strap 235 is shown as permanently attached to the condom 200 near the top of the open end 225. Optionally, however, the restraining strap 235 may be removably attached or completely separate from the condom 200.

Optionally, the semi-fitted condom 200 may also include a restrictive band 245, indicated by dashed lines in FIGS. 6 and 8, around the periphery of the tubular shaft 205. The restrictive band 245 is preferably located at the proximal end of the tubular shaft 205 where it joins to the scrotal sac 210. The restrictive band 245 may be formed by a slight thickening of the wall of the tubular shaft 205 and/or by a slight reduction in the internal diameter of the tubular shaft 205.

FIG. 8 is a side view of the semi-fitted condom 200 of FIG. 6, shown in a fastened state. FIG. 9 is a proximal end view of the semi-fitted condom 200 of FIG. 8 in the fastened state. When fastened, the restraining strap 235 with fixable ends 240 secures the scrotal sac 210 around the genitalia and anchors the condom 200 during use. FIG. 10 illustrates the condom 200 in a rolled condition for packaging and storage or for application.

Figure 11:
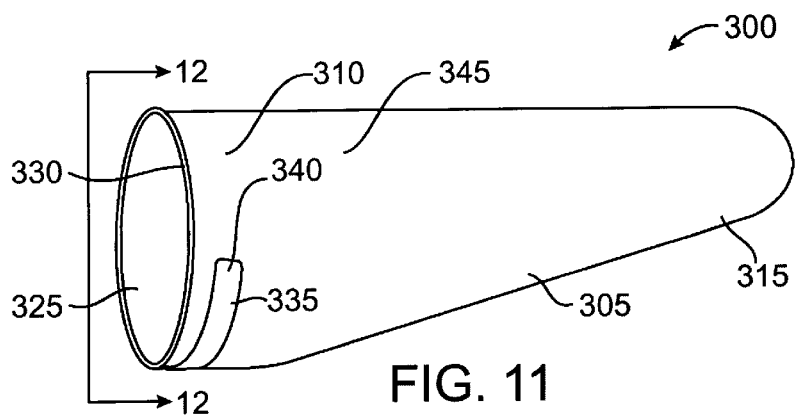
FIG. 11 is a side view of an unfitted version of the condom of the present invention, shown in an unfastened state.
Figure 12:
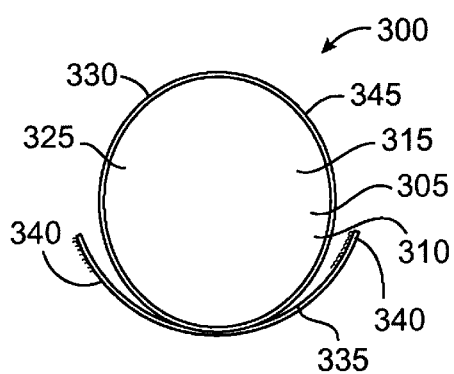
FIG. 12 is a proximal end view of the unfitted condom of FIG. 11 in the unfastened state.

FIGS. 11 through 15 illustrate a third preferred embodiment of the present invention, which is an unfitted version of a condom 300 configured to cover a user's penis and scrotum. FIG. 11 is a side view of the unfitted condom 300 in an unfastened state. FIG. 12 is a proximal end view of the unfitted condom 300 of FIG. 11 in the unfastened state. Rather than having a separate tubular shaft and scrotal sac as in the previously described embodiments, the unfitted condom 300 has a continuously tapered condom body 345 with a rounded, closed distal end 315, characterized by a penile region 305 and a scrotal region 310. The penile region 305 and scrotal region 310 of the tapered condom body 345 provide complete coverage of the penis and scrotum, respectively. In this embodiment, the open end 325 of the unfitted condom 300 preferably represents the maximum diameter of the tapered condom body 345. Alternatively, the open end 325 of the unfitted condom 300 may be somewhat smaller than the maximum diameter of the scrotal region 310, but larger than the diameter of the rounded, closed distal end 315 of the tapered condom body 345, as shown in dashed lines in FIG. 11.

Figure 16:
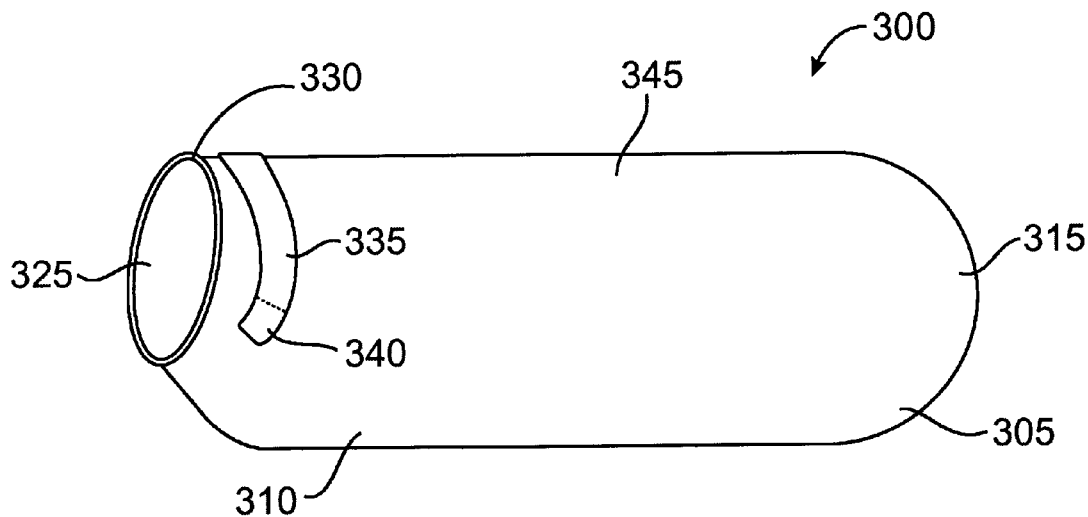
FIG. 16 is a side view of an alternate configuration of the unfitted version of the condom of FIG. 11, shown in an unfastened state.
Figure 17:
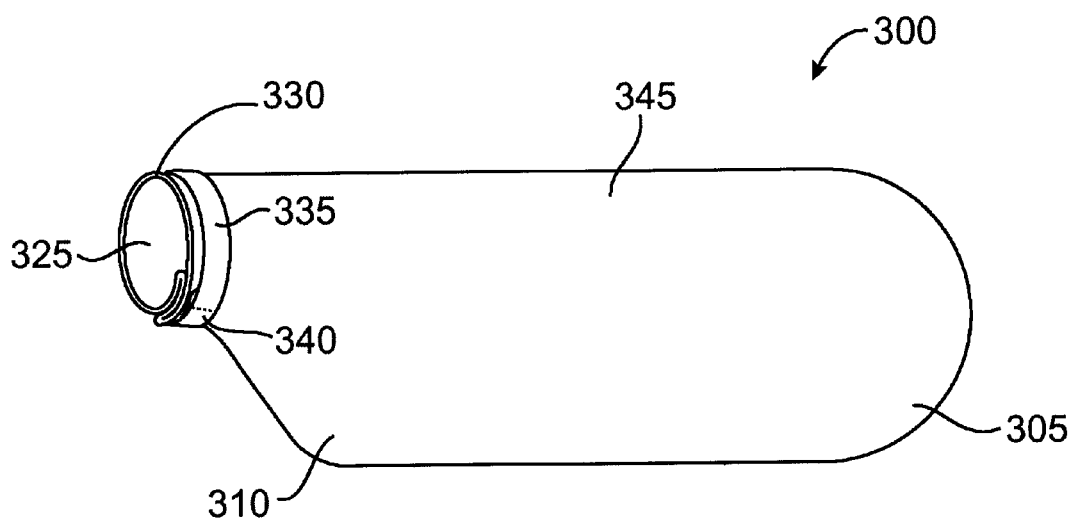
FIG. 17 is a side view of the condom of FIG. 16 in the fastened state.

FIG. 16 is a side view of an alternate configuration of the unfitted version of the condom 300 of FIG. 11, shown in an unfastened state. FIG. 17 is a side view of the unfitted condom 300 of FIG. 16, shown in a fastened state. In this configuration, the condom body 345 is approximately cylindrical rather than tapered, with the penile region 305 and scrotal region 310 having approximately the same diameter. The open end 325 on the scrotal region 310 of the unfitted condom 300 may be approximately the same diameter as the cylindrical condom body 345, or, alternatively, the open end 325 of the unfitted condom 300 may be somewhat smaller than the maximum diameter of the cylindrical condom body 345, as shown.

Preferably, the unfitted condom 300 is made of a highly flexible polymer or elastomer. Because this version of the condom 300 is unfitted, it is not essential that the material of the tapered condom body 345 be highly elastic. Suitable materials include, but are not limited to latex, polyurethane and other natural and synthetic rubbers, as well as many other polymers or elastomers. Preferably, the tapered condom body 345 is manufactured in one piece, such as by dip molding, out of a single material. Alternatively, however, the penile region 305 and a scrotal region 310 may be made of different materials and joined together, for instance by adhesive bonding or by heat welding. Additionally or alternatively, natural membranes or textile fabrics may be used in the construction of the tapered condom body 345 of the condom 300.

The unfitted condom 300 also includes a restraining strap 335 that, when fastened, secures the scrotal region 310 of the tapered condom body 345 and effectively anchors the condom 300 during use. FIGS. 11 and 12 illustrate the restraining strap 335 in position, but not fastened. The restraining strap 335 is preferably constructed of a relatively flat elastic material and has fixable ends 340. The fixable ends 340 of the restraining strap 335 include a fastener, such as corresponding halves of a VELCRO hook-and-loop fastener strip, or an adhesive. In this illustrative embodiment, the restraining strap 335 is shown as permanently attached to the condom 200 at the underside of the open end 325. Optionally, however, the restraining strap 335 may be removably attached or completely separate from the condom 300.

Figure 13:
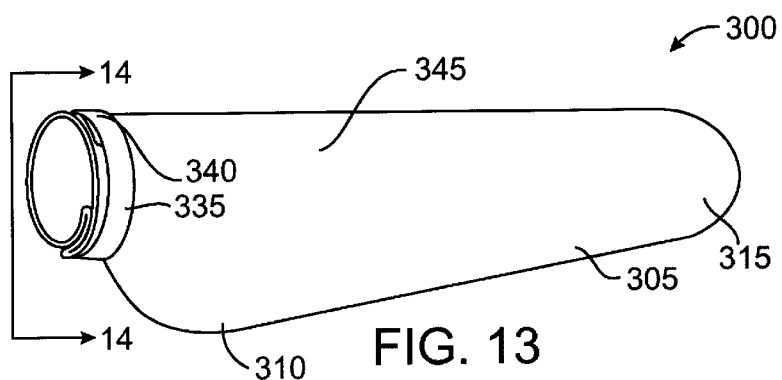
FIG. 13 is a side view of the unfitted condom of FIG. 11, shown in a fastened state.
Figure 14:
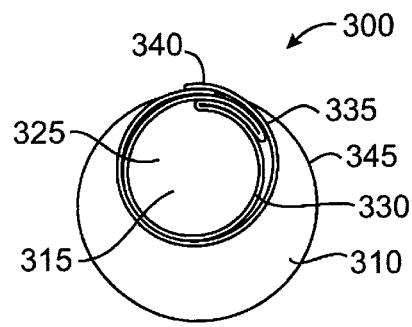
FIG. 14 is a proximal end view of the unfitted condom of FIG. 13 in the fastened state.
Figure 15:
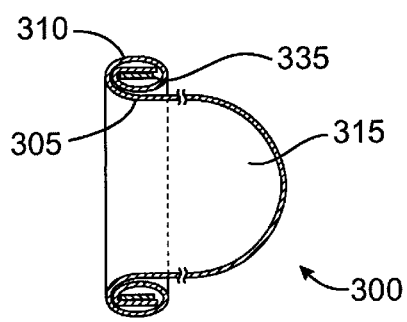
FIG. 15 is a cross section of the unfitted condom of FIG. 11, shown in a rolled state for storage or application.

FIG. 13 is a side view of the unfitted condom 300 of FIG. 11, shown in a fastened state. FIG. 14 is a proximal end view of the unfitted condom 300 of FIG. 13 in the fastened state. When fastened, the restraining strap 335 with fixable ends 340 secures the open end 325 of the tapered condom body 345 around the genitalia and anchors the condom 300 during use. The penile region 305 of the tapered condom body 345 is free to move or slide longitudinally in order to increase sensation to the user, even though the unfitted condom 300 is fully secured by the restraining strap 335. FIG. 15 illustrates the unfitted condom 300 in a rolled condition for packaging and storage or for application.

Other variations of the condom may include rings, bands, ridges, bumps and lumps on the interior or exterior surface of the condom.

Many features have been listed with particular configurations, options, and embodiments. Any one or more of the features described may be added to or combined with any of the other embodiments or other standard devices to create alternate combinations and embodiments.

Although the examples given include many specificities, they are intended as illustrative of only a few possible embodiments of the invention. Other embodiments and modifications will, no doubt, occur to those skilled in the art. Thus, the examples given should only be interpreted as illustrations of some of the preferred embodiments of the invention, and the full scope of the invention should be determined by the appended claims and their legal equivalents.

I claim:

1. A condom configured to cover a user's penis and scrotum, comprising:

a shaft portion, a scrotum portion having one end thereof integrally formed with said shaft portion and another end thereof defining an opening, and a strap member releasably disposed surrounding said opening of said scrotum portion.

2. The condom as set forth in claim 1, wherein said strap member comprises a strap having fixable ends with a hook-and-loop fastener for releasably fastening said strap around said opening of said scrotum portion.

3. The condom as set forth in claim 1, wherein said opening of said scrotum portion includes a stopper ring integrally formed at and surrounding said opening, said stopper ring having a thickness substantially greater than the corresponding thickness of the material forming said scrotum portion.

4. The condom as set forth in claim 3, wherein said shaft portion, said scrotum portion and said stopper ring are formed of a material chosen from a group of materials consisting of polyurethane, latex and rubber.

5. The condom as set forth in claim 3, wherein said strap member is an elastomeric band having fixable ends for releasably fastening said elastomeric band around said opening of said scrotum portion.

6. The condom as set forth in claim 1, wherein said shaft portion is eccentrically formed with said scrotum portion.

7. The condom as set forth in claim 1, wherein said shaft portion and said scrotum portion are configured to tightly fit onto the user.

8. The condom as set forth in claim 1, wherein said shaft portion and said scrotum portion are configured to loosely fit onto the user.

9. The condom as set forth in claim 1, wherein said shaft portion is configured to tightly fit onto the user and said scrotum portion is configured to loosely fit onto the user.

10. A condom configured to cover a user's penis and scrotum, comprising:

a shaft portion having a closed distal end and an open proximal end, a scrotum portion having one end thereof integrally formed with said open proximal end of said shaft portion and another end thereof defining an opening, said scrotum portion having a different circumferential dimension than said shaft portion, said scrotum portion including a stopper ring integrally formed at and surrounding said opening, said stopper ring having a thickness substantially greater than the corresponding thickness of the material forming said scrotum portion, and securing means encompassing said opening of said scrotum portion.

11. The condom as set forth in claim 10 wherein said securing means is an elastomeric band disposed at said opening adjacent to and retained by said stopper ring thereby preventing said elastomeric band from slipping beyond said opening of said scrotum portion.

12. The condom as set forth in claim 10, wherein said securing means comprises a strap having fixable ends with a hook-and-loop fastener for releasably fastening said strap around said opening of said scrotum portion.

13. The condom as set forth in claim 10, wherein said shaft portion and said scrotum portion are configured to tightly fit onto the user.

14. The condom as set forth in claim 10, wherein said shaft portion and said scrotum portion are configured to loosely fit onto the user.

15. The condom as set forth in claim 10, wherein said shaft portion is configured to tightly fit onto the user and said scrotum portion is configured to loosely fit onto the user.

16. The condom as set forth in claim 10, wherein said opening of said scrotum portion is sized to fit loosely around the user's scrotum and said securing means is configured to tighten said opening of said scrotum portion snuggly onto the user.

17. The condom as set forth in claim 10, wherein said opening of said scrotum portion is of a diameter larger than said shaft portion.

18. The condom as set forth in claim 10, wherein said securing means comprises a strap having fixable ends for releasably fastening said strap around said opening of said scrotum portion.

* * * * *